United States Patent
Fay et al.

(10) Patent No.: US 8,523,995 B2
(45) Date of Patent: Sep. 3, 2013

(54) COMPOSITIONS FOR POLYMER BONDING

(75) Inventors: Nigel Fay, Kildare (IE); Eimear M. Fleming, Dublin (IE); Rainer K. Wefringhaus, Hilden (DE); Darren Nolan, Dublin (IE); Brendan J. Kneafsey, Dublin (IE)

(73) Assignees: Henkel AG & Co. KGaA, Duesseldorf (DE); Henkel Ireland Limited, Monheim (DE)

( * ) Notice: Subject to any disclaimer, the term of this patent is extended or adjusted under 35 U.S.C. 154(b) by 56 days.

(21) Appl. No.: 13/416,843

(22) Filed: Mar. 9, 2012

(65) Prior Publication Data

US 2012/0193029 A1 Aug. 2, 2012

Related U.S. Application Data

(63) Continuation of application No. PCT/EP2010/062757, filed on Aug. 31, 2010.

(60) Provisional application No. 61/241,696, filed on Sep. 11, 2009.

(51) Int. Cl.
  *C09J 5/06* (2006.01)
  *C09J 11/06* (2006.01)
  *C09J 183/00* (2006.01)
  *B32B 15/06* (2006.01)
  *C07F 7/10* (2006.01)

(52) U.S. Cl.
  CPC .. *C09J 5/06* (2013.01); *C09J 11/06* (2013.01); *C09J 183/00* (2013.01); *C09J 2203/00* (2013.01); *B32B 15/06* (2013.01); *C07F 7/10* (2013.01)
  USPC ...... 106/287.11; 156/325; 156/326; 156/329; 428/448; 428/450; 428/451; 556/419; 556/421

(58) Field of Classification Search
  USPC ............ 106/287.11; 156/325, 326, 329; 428/448, 450, 451; 556/419, 421
  See application file for complete search history.

(56) References Cited

U.S. PATENT DOCUMENTS

| | | | |
|---|---|---|---|
| 3,542,639 A | 11/1970 | Manino | |
| 4,031,120 A | 6/1977 | Gervase | |
| 6,410,641 B2 * | 6/2002 | Sato et al. | 524/588 |
| 6,423,416 B1 * | 7/2002 | Nanavati | 428/447 |
| 8,153,268 B1 * | 4/2012 | Fay et al. | 428/448 |
| 2009/0181248 A1 | 7/2009 | VanOoij et al. | |

FOREIGN PATENT DOCUMENTS

| WO | 2004078867 | 9/2004 |
|---|---|---|
| WO | 2009118255 | 10/2009 |

OTHER PUBLICATIONS

International Search Report issued in connection with International Patent Application No. PCT/EP2010/062757 mailed on Feb. 15, 2011.

J.J D'Amico, C.C. Tung and L.A. Walker, J. Am. Chem. Soc., 5957 (1959).

Anonymous: "Data Sheet: Methyl Ethyl Ketone (MEK)". Retrieved from the Internet: URL:http://www.panachem.com/msds/methyl_ethyl_ketone_MEK%20spec.pdf on Dec. 10, 2010.

* cited by examiner

*Primary Examiner* — David M Brunsman
(74) *Attorney, Agent, or Firm* — Steven C. Bauman

(57) ABSTRACT

Compositions having a compound comprising at least one alkoxy silane moiety, and at least one moiety selected from a nitrosoaromatic or a nitrosoaromatic precursor and combinations thereof; and an aqueous or water containing carrier medium are provided for use in polymer bonding. The water may allow for substantial hydrolysis of the compound. Suitable polymers may have diene or allylic functionality within the polymer chain, for example an elastomer such as a natural or synthetic rubber. The polymers may be bonded to metals or substrates with hydroxylated surfaces such as glass. The nitrosobenzene precursor may be at least one of a quinone dioxime or a quinone oxime.

16 Claims, No Drawings

COMPOSITIONS FOR POLYMER BONDING

This application is a continuation of PCT/EP2010/062757, filed Aug. 31, 2010.

BACKGROUND

1. Field

Adhesive compositions suitable for use in polymer bonding, for example elastomer bonding, such as rubber bonding applications are provided. One aspect provides adhesive compositions comprising substantially hydrolysed functionalised silane molecules for such bonding applications.

2. Brief Description of Related Technology

Reinforced composite materials play a critical role in the manufacture of high-performance products that need to be lightweight, yet strong enough to take harsh loading and operating conditions. Popular reinforcing materials included wood, glass, metals, quartz and carbon fibres. Composites reinforced with such materials may find utility in the manufacture of a number of structural materials such as aerospace components and racing car bodies.

Polymer to metal and in particular rubber to metal bonding has been practised for many years. There are many applications for formulations which achieve polymer or rubber to metal bonding. Rubber to metal bonding is widely used to bond different metals to a natural or synthetic rubber. Polymer to metal bonding is carried out for many reasons. One aspect of rubber to metal bonding is to combine the structural strength of the metal with the elastomeric properties of the rubber.

Accordingly, metal and polymers such as rubber are often bonded to each other for impact absorption applications, such as in bearings, wheels, shock absorbers, moving arms, etc. Such components can be utilised on a very small scale, for example in PC components or on a very large scale for example in constructions such as bridges and buildings. Noise reduction may also be achieved by utilising metal to rubber bonding. It is accepted that tremendous forces can be experienced by any component that comprises metal and rubber bonded together. Accordingly, it is desirable to provide metal to rubber bonding, which can withstand significant forces, such as compressive or extensive pressures including shocks without having the metal or the rubber separate from each other. There are many other rubber to metal bonding applications, including tyre production where internal wire reinforcements for the tyre are bonded to the rubber of the tyre. Prior art compositions are discussed below.

Glass fibre reinforced composite materials consist of high strength glass fibres embedded in a matrix. For example, Glass Fibre Reinforced Concrete comprises glass fibres embedded in cement-based matrix and may find utility in buildings and other structural edifices. Similarly, Glass Reinforced Plastic comprises glass fibres embedded in a plastic material. Glass Reinforced Plastics are immensely versatile materials which combine to provide lightweight materials with high strength performance. Glass reinforced plastics find utility in a number of different areas from structural engineering to telecommunications.

Elastomer to glass bonding provides an attractive means by which the structural strength of glass can be combined with the elastomeric properties of the elastomer/rubber. Reinforcing fibres such as glass fibres have been used as a reinforcing material for rubber articles such as in rubber belts, tyres and hoses. In particular, glass fibres have been employed to reinforce automotive timing belts, where there is a need for synchronous transfer of power from crankshaft to overhead camshaft without loss of inertia.

Traditionally, such glass cord composites are manufactured by coating individual filaments of glass yarn with specialised coatings, such as resorcinol formaldehyde latex (RFL) formulations. Conventional rubber to metal bonding products are then employed to bond the RFL latex to the rubber via a vulcanisation step.

Traditional rubber-to-metal bonding technology incorporates a two-step system, where in a first step a primer is applied and thereafter in a second step an adhesive is applied. The primer ordinarily consists of solutions or suspensions of chlorinated rubber and phenolic resins containing reactive groups, and also pigments such as titanium dioxide, zinc oxide, and carbon black. The primer is generally applied as a thin layer onto a treated (cleaned) surface of a metallic component such as treated steel component for example a component that has been grit blasted or chemically treated.

The adhesive ordinarily consists of a large range of rubber materials and cross-linkers. These include, but are not restricted to, chlorinated and bromochlorinated rubbers, aromatic nitrosobenzene compounds and bismaleimide as cross-linkers, xylene, perchloroethylene and ethylbenzene as solvents, and also some lead or zinc salts. The adhesive layer is generally the link between the primed metal and the rubber. Other cross-linkers that have been employed in rubber-to-metal bonding technology are aromatic nitroso compounds, such as p-dinitrosobenzene.

Many formulations for rubber to metal bonding exist. For example silanes have been used as corrosion inhibitors and as rubber-to-metal bonding adhesion promoters. U.S. Patent Application Publication No. 2009/0181248 discloses substantially hydrolysed silane solutions, for example bis(trimethoxypropyl)amine and bis(triethoxypropyl)tetrasulfide, for use in a rubber to metal bonding composition. The amino silane and sulphide silane are formulated in a ratio of 1:3 respectively, in an ethanol/water solution.

International (PCT) Patent Publication No. WO2004/078867 to Lord Corporation describes a single coat solvent-based adhesive designed to bond thermoplastic elastomers containing an alkoxy silane/urethane adduct and a chlorinated polymer. Methods of synthesis and formulation are described within this patent document. U.S. Pat. No. 4,031,120 to Lord Corporation describes a composition comprising an isocyanate functional organosilane, in combination with a polyisocyanate and an aromatic nitroso compound. The resulting system is described as a one-coat adhesive for bonding a variety of elastomeric materials to metals and other substrates.

Generally, it is desirable that bonding is achieved during a vulcanisation step like compression moulding, transfer moulding, injection moulding and autoclave heating, for example with steam or hot air. For example, semi-solid rubber can be injected into a mould. The semi-solid rubber is then cross-linked into a fully cured rubber and the bond with the substrate is formed at the same time.

Certain requirements of the curing system are desirable. These include, ease of processing, stability (for example avoiding sedimentation), ease of application, fast drying (to allow handling without fouling), good wetting properties, and good curing strengths. Curing should be achieved independently of the type of elastomer (rubber) employed and also independently of the type of substrate. It will be appreciated that some rubbers are blended materials and accordingly it is desirable that good curing is achieved with such blended materials. Suitably consistent curing is achieved under various process parameters. Durability is also desirable.

Notwithstanding the state of the art it would be desirable to provide compositions to bond polymeric substrates to a variety of substrates (such as metals, glass, and quartz) that remedy some or all of the known deficiencies and/or provide alternatives to the existing technologies so that consumers have more possibilities from which to choose.

SUMMARY

The present invention provides for adhesive compositions and methods of bonding to polymeric substrates. Suitably, the polymer is one with diene and or allylic functionality within the polymer chain. The polymer may have allylic functionality within the polymer chain. For example, the polymer may be an elastomer, such as a natural or synthetic rubber. The synthetic rubber may be a nitrile butadiene rubber. The synthetic rubber may be a hydrogenated nitrile butadiene rubber (HNBR).

In one aspect, the present invention provides for an adhesive composition comprising:
(i) a compound comprising:
a) at least one alkoxy silane moiety; and
b) at least one moiety selected from an aromatic nitroso or an aromatic nitroso precursor and combinations thereof; and
(ii) a carrier for the compound, the carrier comprising at least 0.1% w/w water.

The carrier comprising at least 0.1% w/w water may allow for hydrolysis of the compound comprising the at least one alkoxy silane moiety. As used herein hydrolysis of the compound refers to hydrolysis of the alkoxy silane moiety, i.e., hydrolysis of any alkoxy moiety to yield a hydroxy moiety. At least one alkoxy moiety in the compound may be hydrolysed to ensure good bonding. Advantageously, hydrolysis of the compound prior to bonding may result in improved adhesion. Hydrolysis of the compound prior to bonding may result in improved bond strengths. Hydrolysis of the compound prior to bonding may result in improved bond strengths in bonding a polymeric substrate having diene and or allylic functionality within the polymer chain to a metal or hydroxylated surface.

The compositions of the present invention may find utility in bonding a substrate to an elastomer. The composition of the present invention may find utility in bonding a substrate to a natural or synthetic rubber. The synthetic rubber may be a nitrile butadiene rubber. The synthetic rubber may be HNBR.

The substrate may be a metal or a hydroxylated surface. As used herein the term hydroxylated surface refers to any substrate with a surface comprising an atom bonded to a hydroxy group. Suitable non-limiting examples include, a hydrous metal oxide, glass substrates comprising surface Si—OH bonds or clay substrates comprising surface Al—OH bonds. Suitable hydroxylated surfaces include those of silicates, aluminates, germanates and combinations thereof The hydroxylated surface may be a silicate, an aluminate or combinations thereof As used herein, the term silicate refers to substrates comprising Si—OH bonds. The term aluminate refers to substrates having Al—OH bonds and the term germinate refers to substrates having Ge—OH bonds. For example, the hydroxylated surface may be one of glass such as glass fibres, quartz, clays, talcs, zeolites, porcelains, ceramics, and silicon substrates such as silicon wafers and combinations thereof.

Many different metals may be treated with the composition of the present invention. Suitable metals include, but are not limited to, zinc and zinc alloys such as zinc-nickel and zinc-cobalt alloys, metal substrates having zinc-containing coatings, steel and in particular cold rolled and carbon steel, aluminium and aluminium alloys, copper and copper alloys such as brass, and tin and tin alloys including metal substrates having tin-containing coatings.

Within the context of this specification the term aromatic nitroso moiety refers to an aromatic moiety having at least one nitroso group. Similarly, the term aromatic nitroso precursor moiety refers to any compound that is capable of being transformed into an aromatic nitroso moiety with at least one nitroso group. The term aromatic comprises both fused and non-fused aromatic rings. For example, a non-limiting selection of fused and non-fused aromatic nitroso moieties embraced by the present invention are detailed below:

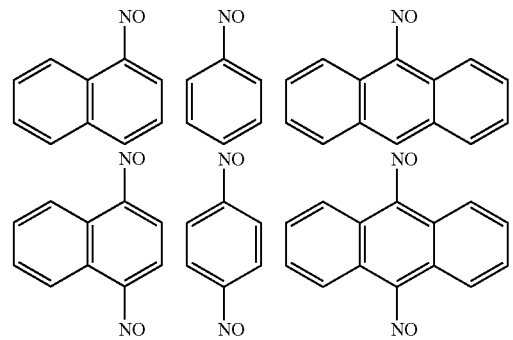

As will be appreciated by a person skilled in the art, the nitroso structures disclosed above may optionally be substituted one or more times, for example with at least one of $C_1$-$C_{20}$ alkyl, $C_1$-$C_{20}$ cycloalkyl, $C_1$-$C_{20}$ alkoxy, $C_7$-$C_{20}$ aralkyl, $C_7$-$C_{20}$ alkaryl, $C_6$-$C_{20}$ arylamine, $C_6$-$C_{20}$ arylnitroso, cyano, amino, hydroxy, halogen and combinations thereof Such substitutions are possible provided there is no interference with effective bonding or curing of the compositions.

The compounds used in the composition of the present invention may assist in the formation of polymer to glass bonds or metal bonds. The polymer may be an elastomer such as a natural or synthetic rubber. The synthetic rubber may be a nitrile butadiene rubber. The synthetic rubber may be HNBR. The compounds can be easily applied at the interface between the polymer and the glass or metal substrate and may assist in developing strong and durable bonds during the curing process.

The so-described compositions may result in a number of advantages. For example, a one-part adhesive system may be formulated. Such systems are readily applied to substrates in a single step using convenient and conventional techniques, for example spraying or dipping. Compositions as so provided may have reduced toxicity as compared to conventional dinitrosobenzene formulations. Compositions as so provided can also achieve excellent bond strengths.

The adhesive systems of the present invention can be applied to an unvulcanised rubber substrate (as distinct from a metal or glass substrate), prior to vulcanisation and bond formation, and upon subsequent vulcanization a bond results. The composition may be applied to a metal or a hydroxylated surface. This means that the adhesive system may be applied to either the polymeric substrate such as a rubber or a metal or glass substrate. Conventional systems do not form a bond if applied in this manner.

The aromatic nitroso precursor moiety may comprise any aromatic oxime, aromatic dioxime and combinations thereof For example, the aromatic nitroso precursor moiety may be the mono- or dioxime of a compound selected from:

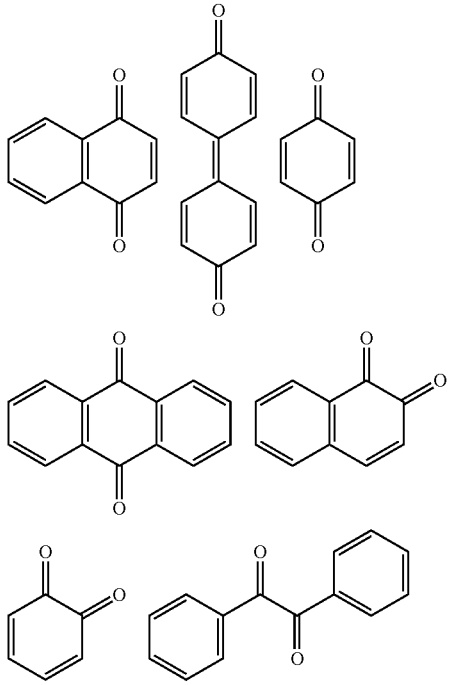

As will be appreciated by a person skilled in the art, the diketone structures disclosed above may optionally be substituted one or more times, for example with at least one of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_6$-$C_{20}$ arylamine, $C_6$-$C_{20}$ arylnitroso, cyano, amino, hydroxy, halogen and combinations thereof Such substitutions are possible provided there is no interference with effective bonding or curing of the compositions, for example, with the generation of an aromatic nitroso compound in-situ.

The aromatic nitroso moiety of the compound of the present invention may comprise a nitrosobenzene moiety. The nitrosobenzene moiety may be a mononitrosobenzene, a dinitrosobenzene, or combinations thereof Similarly, the aromatic nitroso precursor moiety of the composition of the present invention may comprise a nitrosobenzene moiety precursor. The nitrosobenzene precursor may be a mononitrosobenzene precursor, a dinitrosobenzene precursor, or combinations thereof. It will be appreciated that the nitrosobenzene precursor may form a nitrosobenzene structure in-situ. The nitrosobenzene precursor may be at least one of a quinone dioxime or a quinone oxime.

As will be appreciated by a person skilled in the art, references to nitrosobenzene and nitrosobenzene precursor moieties include nitrosobenzene and nitrosobenzene precursor moieties that may optionally be substituted one or more times with at least one of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_6$-$C_{20}$ arylamine, $C_6$-$C_{20}$ arylnitroso, cyano, amino, hydroxy, halogen and combinations thereof Such substitutions are possible provided there is no interference with effective bonding or curing of the compositions. For example, provided there is no interference with the generation of a nitrosobenzene moiety in-situ.

The silane moiety may be of the structure:

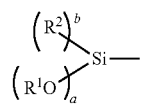

where 'a' can be 1-3 and 'b' can be 0-2, wherein a+b=3 and at least one alkoxy group is present;

$R^1$ can be selected from H, $C_1$-$C_{24}$ alkyl, $C_3$-$C_{24}$ acyl, preferably from $C_1$-$C_4$ alkyl;

wherein when a≧1 at least one $R^1$ is not hydrogen; and $R^2$ can be selected from $C_1$-$C_{24}$ alkyl and $C_3$-$C_{24}$ acyl, preferably from $C_1$-$C_4$ alkyl.

In one embodiment, a is 3 and $R^1$ is $C_1$-$C_{24}$ alkyl. $R^1$ may be $C_1$-$C_4$ alkyl and a may be 3.

The compounds may be reaction products derived from an isocyanate or isothiocyanate and an active hydrogen compound, such as —$NH_x$ (where x=1 or 2), —SH, or —OH. In this manner the so-described compounds should contain at least one linkage described by:

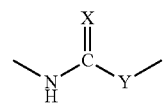

where X can be S or O, and Y includes —$NH_x$ (where x=1 or 2), —S, or —O.

The general structure for these compounds is shown below:

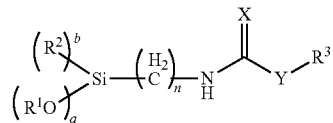

where 'a' can be 1-3 and 'b' can be 0-2; wherein a+b=3 and at least one alkoxy group is present;

$R^1$ can be selected from H, $C_1$-$C_{24}$ alkyl, $C_3$-$C_{24}$ acyl, preferably from $C_1$-$C_4$ alkyl and where when a≧1 at least one $R^1$ is not hydrogen;

$R^2$ can be selected from $C_1$-$C_{24}$ alkyl and $C_3$-$C_{24}$ acyl, preferably from $C_1$-$C_4$ alkyl;

n can be 1-10;

X can be O or S;

Y can be —O, —S, or —$NH_x$ (where x=1 or 2); and $R^3$ may be a moiety comprising nitrosoaromatic, or a nitrosoaromatic precursor as defined herein.

$R^3$ may be a moiety comprising nitrosobenzene, quinone dioxime or quinone oxime.

$R^1$ may be selected from $C_1$-$C_{24}$ alkyl, $C_3$-$C_{24}$ acyl. $R^1$ may be selected from $C_1$-$C_{24}$ alkyl, $C_3$-$C_{24}$ acyl and 'a' may be 3. X may be O. Y may be O or —$NH_x$ (where x=1). Y may be O. X and Y may be O. $R^1$ may be selected from $C_1$-$C_4$ alkyl, X may be O and 'a' is 3. $R^1$ may be selected from $C_1$-$C_4$ alkyl, X may be O, Y may be O and 'a' may be 3. $R^1$ may be selected from $C_1$-$C_4$ alkyl, X may be O, Y may be —$NH_x$ (where x=1) and 'a' may be 3. $R^1$ may be selected from $C_1$-$C_4$ alkyl, X may be O, Y may be O, 'a' may be 3 and $R^3$ may be a moiety comprising nitrosobenzene.

Structures for R³, showing the linkage through 'Y', can include:

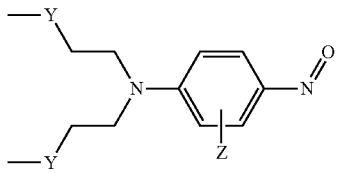

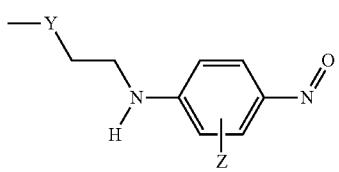

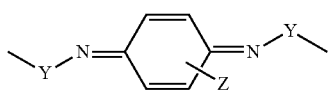

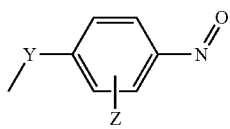

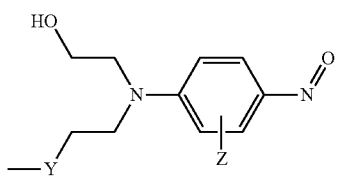

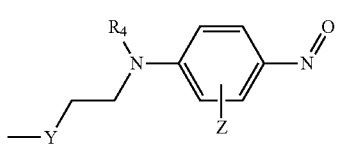

where $R_4$ can be $C_1$ to $C_{10}$; and

Z indicates that the rings of the above structures can optionally be mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_5$-$C_{20}$ arylamine, $C_5$-$C_{20}$ arylnitroso, amino, hydroxy, halogen and combinations thereof, and further where the substituents can either be the same or different on each carbon atom of the ring. Such substitutions may be possible provided there is no interference with effective bonding or curing of the compositions. For example, provided there is no interference with the generation of a nitrosobenzene compound in-situ.

The compound utilised in the composition of the present invention may have the general structure:

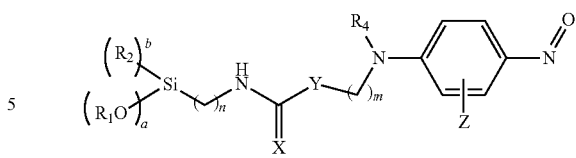

where 'a' can be 1-3 and 'b' can be 0-2; wherein a+b=3 and at least one alkoxy group is present;

$R^1$ can be selected from H, $C_1$-$C_{24}$ alkyl, $C_3$-$C_{24}$ acyl, preferably from $C_1$-$C_4$ alkyl and where when a≧1 at least one $R^1$ is not hydrogen; and $R^2$ can be selected from $C_1$-$C_{24}$ alkyl and $C_3$-$C_{24}$ acyl, preferably from $C_1$-$C_4$ alkyl;

m and n can be the same or different and can be 1-10;

X can be O or S;

Y can be —O—, —S—, or —NH;

$R_4$ can be $C_1$ to $C_{10}$; and

Z indicates that the rings of the above structures can optionally be mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_5$-$C_{20}$ arylamine, $C_5$-$C_{20}$ arylnitroso, amino, hydroxy, halogen and combinations thereof, and further wherein the substituents can either be the same or different on each carbon atom of the ring. Such substitutions may be possible provided there is no interference with effective bonding or curing of a bonding composition comprising the compound.

$R^1$ may be selected from $C_1$-$C_{24}$ alkyl or $C_3$-$C_{24}$ acyl. $R^1$ may be selected from $C_1$-$C_{24}$ alkyl, $C_3$-$C_{24}$ acyl and 'a' may be 3. X may be O. Y may be O or NH. Y may be O. X and Y may be O. n may be $C_2$-$C_5$ alkyl, m may be $C_2$-$C_5$ alkyl. $R^1$ may be selected from $C_1$-$C_4$ alkyl, X may be O and 'a' is 3. $R^1$ may be selected from $C_1$-$C_4$ alkyl, X may be O, Y may be O and 'a' may be 3. $R^1$ may be selected from $C_1$-$C_4$ alkyl, X may be O, Y may be NH and 'a' may be 3. $R^1$ may be selected from $C_1$-$C_4$ alkyl, X may be O, Y may be O, 'a' may be 3 and $R^4$ may be $C_1$ to $C_{10}$.

The compound in the composition of the present invention may have the general structure:

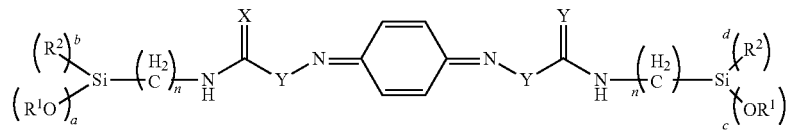

where n can be 1-10;

'a' can be 1-3 and 'b' can be 0-2; wherein a+b=3 and at least one alkoxy group is present;

c can be 'a' or 1 to 3; d can be 'b' or 1 to 3;

$R^1$ can be selected from H, $C_1$-$C_{24}$ alkyl, $C_3$-$C_{24}$ acyl, preferably from $C_1$-$C_4$ alkyl and where when a≧1 at least one $R^1$ is not hydrogen;

$R^2$ can be selected from $C_1$-$C_{24}$ alkyl and $C_3$-$C_{24}$ acyl, preferably from $C_1$-$C_4$ alkyl;
X can be O or S; and
Y can be —O, —S, or —$NH_x$ (where x=1 or 2).

$R^1$ may be selected from $C_1$-$C_{24}$ alkyl, $C_3$-$C_{24}$ acyl. $R^1$ may be selected from $C_1$-$C_{24}$ alkyl, $C_3$-$C_{24}$ acyl and 'a' may be 3. X may be O. Y may be O or —$NH_x$ (where x=1). Y may be O. X and Y may be O. $R^1$ may be selected from $C_1$-$C_4$ alkyl, X may be O and 'a' is 3. $R^1$ may be selected from $C_1$-$C_4$ alkyl, X may be O, Y may be O and 'a' may be 3. $R^1$ may be selected from $C_1$-$C_4$ alkyl, X may be O, Y may be —$NH_x$ (where x=1) and 'a' may be 3. $R^1$ may be selected from $C_1$-$C_4$ alkyl, X may be O, Y may be O, n may be 3 and 'a' may be 3.

In a further embodiment, the compound of the composition of the present invention may be an oligomeric or co-oligomeric compound of the general structure:

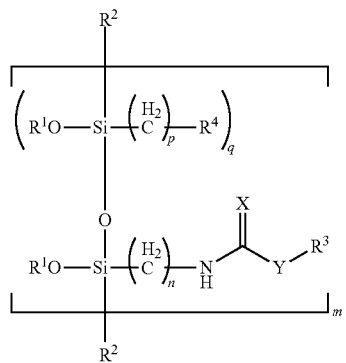

where m can be 1-100; n can be 110; p can be 110; q can be 0-50; and if q=0, m≧2;

$R^1$ can be selected from H, $C_1$-$C_{24}$ alkyl, $C_3$-$C_{24}$ acyl, and preferably from $C_1$-$C_4$ alkyl;
$R^2$ can be selected from $OR^1$, $C_1$-$C_{24}$ alkyl and $C_3$-$C_{24}$ acyl, and where when $R^2$=$OR^1$ at least one $R^1$ is not hydrogen;
$R^4$ can be selected from acrylate, aldehyde, amino, anhydride, azide, maleimide, carboxylate, sulphonate, epoxide, ester functional, halogens, hydroxyl, isocyanate or blocked isocyanate, sulfur functional, vinyl and olefin functional, or polymeric structures;
X can be O or S;
Y can be —O, —S, or —$NH_x$ (where x=1 or 2); and
$R^3$ may be a moiety comprising nitrosoaromatic, or a nitrosoaromatic precursor as defined herein.

$R^3$ may be a moiety comprising nitrosobenzene, quinone dioxime or quinone oxime.

$R^1$ may be selected from $C_1$-$C_{24}$ alkyl, $C_3$-$C_{24}$ acyl. $R^1$ may be selected from $C_1$-$C_{24}$ alkyl, $C_3$-$C_{24}$ acyl and $R^2$ may be $OR^1$. X may be O. Y may be O or —$NH_x$ (where x=1). Y may be O. X and Y may be O. $R^1$ may be selected from $C_1$-$C_4$ alkyl, X may be O and $R^2$ may be $OR^1$. $R^1$ may be selected from $C_1$-$C_4$ alkyl, X may be O, Y may be O and $R^2$ may be $OR^1$. $R^1$ may be selected from $C_1$-$C_4$ alkyl, X may be O, Y may be —$NH_x$ (where x=1) and $R^2$ may be $OR^1$. $R^1$ may be selected from $C_1$-$C_4$ alkyl, X may be O, Y may be O, n may be 3, $R^2$ may be $OR^1$ and $R^3$ may be a moiety comprising nitrosobenzene. $R^1$ may be selected from $C_1$-$C_4$ alkyl, X may be O, Y may be O, n may be 3, $R^2$ may be $OR^1$, $R^3$ may be a moiety comprising nitrosobenzene, q may be 0, and m may be ≧2. $R^1$ may be selected from $C_1$-$C_4$ alkyl, X may be O, Y may be O, n may be 3, $R^2$ may be $OR^1$, $R^3$ may be a moiety comprising nitrosobenzene, q may be 0, m may be ≧2, and $R^4$ may be vinyl or ester.

Specific examples of compounds used in the compositions of the present invention may include the following:

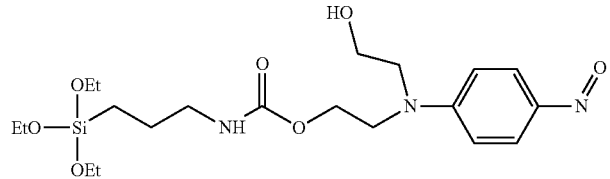

(A)

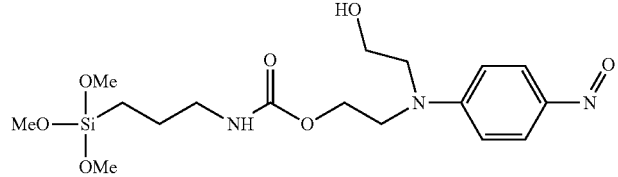

(B)

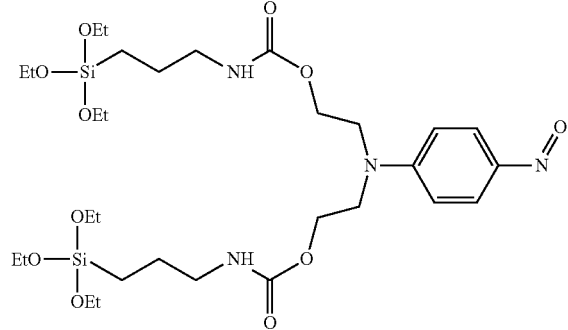

(C)

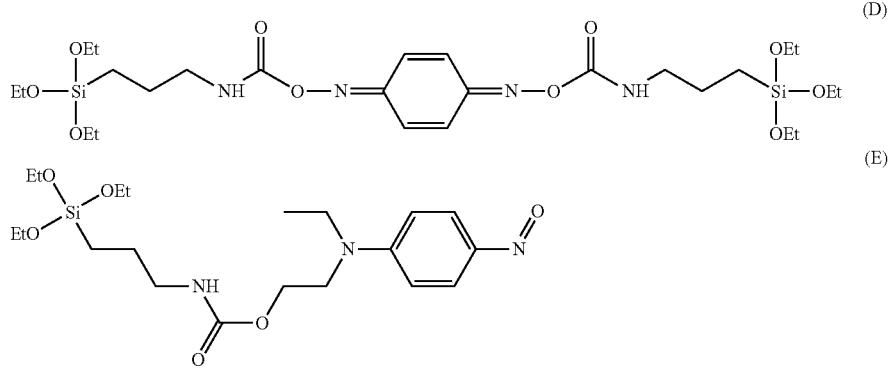

The composition of the present invention may comprise the following compound:

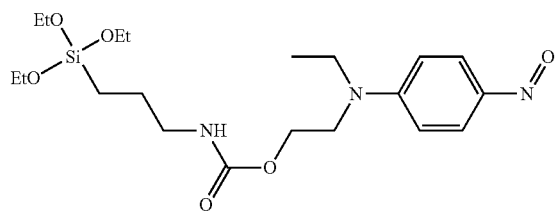

The reaction scheme for the synthesis of compound (A) is below (all compounds are made in an analogous method).

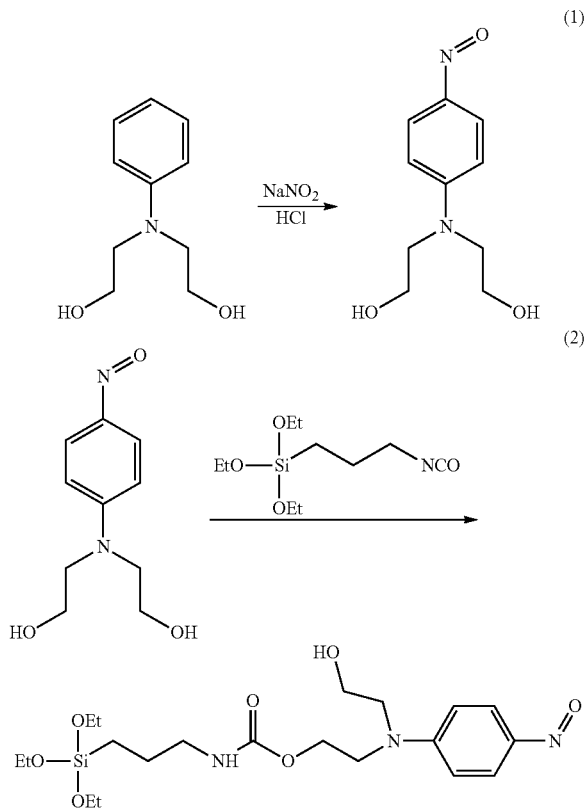

The compound comprising the at least one alkoxy silane moiety and the at least one moiety selected from an aromatic nitroso or an aromatic nitroso precursor (also referred to as a nitrososilane) may be present in an amount of 1 to 20% w/w of the total composition. Suitably, the at least one aromatic nitroso compound precursor may be present in an amount of 1 to 15% w/w, for example 4 to 12% w/w. The at least one aromatic nitroso compound precursor may be present in 6% w/w of the total composition.

The presence of water in the composition of the present invention facilitates substantial hydrolysis of the nitrososilane (i.e., the compound utilised in the composition of the present invention). At least one alkoxy moiety in the compound may be hydrolysed to ensure good bonding. The carrier may further comprise an organic solvent. Desirably, the organic solvent is miscible with water. This allows for efficient dissolution of and hydrolysis of the nitrososilane. The organic solvent may be selected from the group consisting of alcohols, carboxylic acids, acetone, acetonitrile, and tetrahydrofuran. The organic solvent may be an alcohol. Suitable alcohols include, without limitation, methanol, ethanol, propanol and isomers thereof, butanol and isomers thereof, and pentanol and isomers thereof.

The carrier of the composition of the present invention may comprise between 0.1-100% w/w water. The carrier of the composition of the present invention may comprise between 0.5-50% w/w water. The carrier of the composition of the present invention may comprise between 1-20% w/w water. Suitably, a carrier comprising about 5% w/w water may substantially hydrolyse the nitrososilanes.

Desirably, the carrier consists of water and an alcohol. An alcohol:water carrier provides for dissolution of the nitrososilane in the carrier, thereby enabling uniform application of the compound as a film or coating to a target substrate. Uniform application of the nitrososilane compound as part of a composition may result in improved bonding.

Compositions of the present invention may find utility in any application where it is desirable to form an aromatic nitroso moiety in-situ. Similarly, compositions of the present invention may find utility in any application where it is desirable to form an aromatic dinitroso moiety in-situ. It will be appreciated that within these compositions the compound can react in-situ to form a nitrosobenzene moiety. It is also contemplated that the compound can react in-situ to form a dinitrosobenzene moiety. For example, for particularly good bonding it may be desirable for the compound to react in-situ to form a para-nitrosophenol moiety.

Compositions of the present invention may be one-part compositions or two-part compositions.

The composition of the present invention may further comprise an acid. Suitable acids include organic acids. For example, acetic acid, oxalic acid, formic acid, and propionic acid.

Hydrolysis of alkoxy silanes (formation of silanol groups, i.e. SiOH) will generally occur efficiently within the pH range of 3-7. At a pH above or below this range, silane condensation may occur by a process where the silanol self-condenses to form a siloxane. During this process the hydroxyl molecules of the adjacent molecules react with one another to eliminate molecules of water and form a cross-linked siloxane structure containing —Si—O—Si—O—Si— functionality.

To accelerate silane hydrolysis and inhibit silane condensation during the hydrolysis step, the pH of the silane solution may be maintained below about 7 and preferably in the mildly acidic range from about 4 to 6.5.

The compositions of the present invention may further comprise conventional additives such as fillers, pigments, stabilisers, and moisture scavengers, subject to the additives not interfering with effective curing of the compositions. The composition may comprise carbon blacks. The carbon blacks may be acidic or basic. The composition may comprise silica. The composition may comprise polyvinyl butyral resin.

Compositions of the present invention may comprise additional silanes. These silanes may be of the general formula:

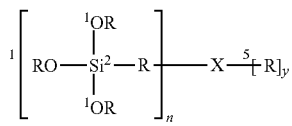

where:
n is either 1 or 2;
y=(2−n)
each $R^1$ can be selected from $C_1$-$C_{24}$ alkyl or $C_2$-$C_{24}$ acyl;
each $R^2$ can be selected from $C_1$-$C_{30}$ aliphatic groups, or substituted or unsubstituted $C_6$-$C_{30}$ aromatic groups;
$R^5$ can be selected from hydrogen, $C_1$-$C_{10}$ alkylene, $C_1$-$C_{10}$ alkylene substituted with one or more amino groups, $C_2$-$C_{10}$ alkenylene substituted with one or more amino groups, $C_6$-$C_{10}$ arylene, or $C_7$-$C_{20}$ alkarylene;
X—$R^5$ is optional and X is either:

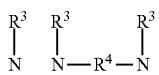

where each $R^3$ can be selected from hydrogen, $C_1$-$C_{30}$ aliphatic groups, or $C_6$-$C_{30}$ aromatic groups; and
$R^4$ can be selected from $C_1$-$C_{30}$ aliphatic groups, or $C_6$-$C_{30}$ aromatic groups; and
where when n=1, at least one of $R^3$ and $R^5$ is not hydrogen.

In one embodiment, X—$R^5$ is present. $R^1$ can be selected from $C_1$-$C_{24}$ alkyl, $R^2$ can be selected from $C_1$-$C_{30}$ aliphatic groups, X can be N—$R^3$ and $R^5$ can be selected from hydrogen or $C_1$-$C_{10}$ alkylene. As will be appreciated, when X—$R^5$ is absent the silane may be of the general formula (wherein $R_1$ and $R_2$ are as defined above):

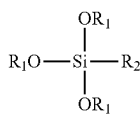

Preferred silanes include bis-silyl silanes such as those having two trisubstituted silyl groups. The substituents may be individually chosen from $C_1$-$C_{20}$ alkoxy, $C_6$-$C_{30}$ aryloxy and $C_2$-$C_{30}$ acyloxy. Suitable bis-silyl silanes for use within the present invention include:

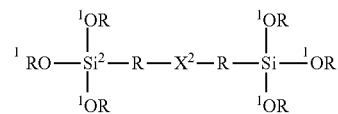

where:
each $R^1$ can be selected from $C_1$-$C_{24}$ alkyl or $C_2$-$C_{24}$ acyl;
each $R^2$ can be selected from $C_1$-$C_{20}$ aliphatic groups or $C_6$-$C_{30}$ aromatic groups;
X is optional and is either:

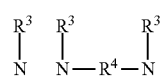

where each $R^3$ can be selected from hydrogen, $C_1$-$C_{20}$ aliphatic groups, or $C_6$-$C_{30}$ aromatic groups; and
$R^4$ can be selected from $C_1$-$C_{20}$ aliphatic groups or $C_6$-$C_{30}$ aromatic groups.

In one embodiment, X is present. $R^1$ can be selected from $C_1$-$C_{24}$ alkyl, $R^2$ can be selected from $C_1$-$C_{30}$ aliphatic groups, and X can be N—$R^3$. As will be appreciated, when X is absent the bis-silane may be of the general formula (wherein $R^1$ and $R^2$ are as defined above):

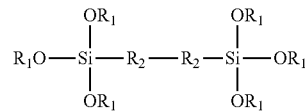

Examples of some bis-silyl aminosilanes embraced by the present invention include: bis-(trimethoxysilylpropyl)amine, bis-(triethoxysilylpropyl)amine, bis-(triethoxysilylpropyl) ethylene diamine, N-[2-(vinylbenzylamino)ethyl]-3-aminopropyltrimethoxy silane, and aminoethyl-aminopropyltrimethoxy silane.

Such silanes may be included in the range from 1:3 to 3:1 relative to the nitrososilane compounds (stoichiometrically). Such mixing of silanes and nitrososilanes can result in excellent bonding to rubber substrates.

The silane may be present in an amount of 1 to 10% w/w of the total composition. Suitably, the silane may be present in an amount of 1 to 5% w/w, for example 1 to 3% w/w. The silane may be present in about 3% w/w of the total composition.

In particular, the inclusion of the amino bis(propyltrimethoxysilane) in addition to the nitrososilane significantly enhances the bond strength to rubber. It is thought that the amino bis(propyltrimethoxysilane) has multiple functions within the formulation. This includes aiding the film forming and "wetting" of the metal surface.

Generally, the final solution applied to the target substrate may vary in the total silane concentration and ratio (silane to nitrososilane) over a wide range and still provide beneficial results. The final solution should contain a total silane concentration of at least approximately 0.1% by volume, i.e., the concentration of the combination of silanes and nitrososilanes in the final solution. Solutions having a total silane concentration of between about 0.1% and about 10% by volume generally provide strong bonding without waste of valuable silanes.

In a further aspect, the present invention provides for a method of bonding two substrates together, the method comprising:
1. substantially hydrolysing a compound comprising:
   a) at least one alkoxy silane moiety; and
   b) at least one moiety selected from an aromatic nitroso or an aromatic nitroso precursor and combinations thereof;
2. applying the substantially hydrolysed compound of step 1 to at least one substrate; and
3. mating the first and second substrates so as to form a bond therebetween.

At least one alkoxy moiety in the compound may be hydrolysed to ensure good bonding. As will be appreciated by a person skilled in the art, the order of steps 1 and 2 is inconsequential. For example, the product may be applied to at least one substrate and then hydrolysed, or the product may be hydrolysed prior to application to the at least one substrate. The method may further comprise the step of heating subsequent to mating the first and second substrates. Advantageously, heating may increase the rate of bond formation. Heating may improve bond strength.

In yet a further aspect, the present invention provides for a method of bonding two substrates together comprising:
1. providing a composition (according to the present invention) comprising:
   (i) a compound comprising:
      a) at least one alkoxy silane moiety; and
      b) at least one moiety selected from an aromatic nitroso or an aromatic nitroso precursor and combinations thereof; and
   (ii) a carrier for the compound, the carrier comprising at least 0.1% w/w water;
2. heating the composition; and
3. applying a composition to a bonding surface of at least one of the substrates and bringing the bonding surfaces of the substrates together.

As will be appreciated by a person skilled in the art, the order of steps 2 and 3 is inconsequential. For example, the composition may be applied to at least one substrate and then heated, or the composition may be heated prior to application to the at least one substrate.

The provision of heat may aid in the hydrolysis of the alkoxy silane moiety of the compound. The composition may be heated to a temperature between 30-100° C. Suitably, the composition may be heated to a temperature between 40-60° C. The composition may be heated to 50° C. The composition may be heated for between 1-2 hours. The composition may be heated for up to 2 hours. The composition may be applied directly to the target substrate. The composition may be cooled prior to application to the target substrate.

The composition may be applied to a target substrate as a thin film or coating. This may allow for uniform (or even) application of the composition to the target substrate. Uniform application of the composition to a target substrate may allow for improved bonding.

The method may further comprise the step of heating subsequent to bringing the surfaces together. Advantageously, heating may increase the rate of bond formation. Heating may improve bond strength.

The method of the present invention may additionally comprise the step of cleaning, for example abrasively cleaning, such as blasting, for example grit-blasting the substrate prior to application of the composition thereto.

In the methods of the present invention a first substrate may be a metal or a hydroxylated surface. Suitable metals include, but are not limited to, zinc and zinc alloys such as zinc-nickel and zinc-cobalt alloys, metal substrates having zinc-containing coatings, steel and in particular cold rolled and carbon steel, aluminium and aluminium alloys, copper and copper alloys such as brass, and tin and tin alloys including metal substrates having tin-containing coatings.

As used herein the term hydroxylated surface refers to any substrate with a surface comprising an atom bonded to a hydroxy group. Suitable non-limiting examples include a hydrous metal oxide, glass substrates comprising surface Si—OH bonds or clay substrates comprising surface Al—OH bonds. Suitable hydroxylated surfaces include those of silicates, aluminates, germanates and combinations thereof. The hydroxylated surface may be a silicate, an aluminate or combinations thereof. As used herein, the term silicate refers to substrates comprising Si—OH bonds. The term aluminate refers to substrates having Al—OH bonds and the term germinate refers to substrates having Ge—OH bonds. For example, the hydroxylated surface may be one of glass such as glass fibres, quartz, clays, talcs, zeolites, porcelains, ceramics, and silicon substrates such as silicon wafers and combinations thereof.

In the methods of the present invention a second substrate may comprise a polymer. The polymer may comprise alkene and/or allylic functionality within the polymer chain. For example, diene and/or allylic functionality may be present within the polymer chain. Suitably, the polymer may comprise allylic functionality. Suitable polymers may include elastomers. Suitable elastomers may comprise natural or synthetic rubbers. The synthetic rubber may be a nitrile butadiene rubber. The synthetic rubber may be HNBR. The polymer may be a $C_2$-$C_{1,000,000}$ polymer, such as a $C_2$-$C_{10,000}$ polymer.

For example, a first substrate may be constructed from a natural or synthetic rubber to be bonded to another substrate. The synthetic rubber may be a nitrile butadiene rubber. The synthetic rubber may be HNBR. The other or second substrate may be a metallic substrate. Generally, the alkoxy silane moiety of the compound will anchor to a metal surface. The moiety selected from an aromatic nitroso or an aromatic nitroso precursor will generally become anchored to the rubber. Similarly, the moiety selected from a nitrosobenzene or a nitrosobenzene precursor will generally become anchored to the rubber. Accordingly, each end of the molecule is functionalised and assists in bonding the materials together with a strong and durable bond.

Thus, a metal coated with an adhesive composition as so described may be adhered to a polymeric material, for example a rubber composition, by applying the polymeric material in an uncured state onto the metal coated with the adhesive composition and curing the polymeric material thereon to bond it to the metal. In the case of a rubber polymeric material the uncured rubber may be vulcanized via heat and pressure over a period of time to cure the rubber, resulting in bonding of the rubber to the metal.

Such bonding to metal and or hydroxylated surfaces is achieved through the nitroso groups which are capable of reacting with polymers. The polymer may comprise alkene/allylic functionality within the polymer chain. For example, diene or allylic functionality within the polymer chain.

Alternatively, suitable polymers are those capable of reacting with nitroso groups so as to provide cross-links therebetween. Such a reaction produces a variety of cross-links, for example between the nitroso group and a rubber material. The materials of the invention are thought to reduce free nitroso groups as the nitroso group is within a molecular structure. In the reaction of the nitroso group and the silane, the nitroso may react with allylic functionality within a natural rubber while the silane forms a bond with the second substrate, such as a hydroxylated surface or metal.

Excellent adhesion between polymeric materials, such as rubber compositions, and metals or hydroxylated surfaces, with minimal waste of silane solution, may be realized through the use of the compounds and compositions as so described. With reference to their use in adhesive applications, the compositions of the present invention are generally thinner than the compositions present in the traditional adhesive systems for rubber bonding, without any loss in performance characteristics.

In a further aspect the present invention provides for a substrate having a composition according to the present invention pre-applied thereto for subsequent bonding to a second substrate. As used herein, the term pre-applied indicates that the composition of the present invention may be applied to a substrate such that it remains secured thereto, and the resulting pre-treated substrate is suitable for storage. The composition should retain its efficacy over time. The pre-treated substrate may be stored for subsequent bonding to a second substrate. Advantageously, substrates can be coated with the composition in a pre-treatment process, optionally stored, and subsequently utilised in (automated) manufacturing processes. The composition may be pre-applied to a polymeric substrate (such as an elastomer, for example a natural or synthetic rubber), a metal or a hydroxylated surface. The composition may be pre-applied to a metal or a hydroxylated surface.

In a further aspect, the present invention provides for a container having therein a composition (according to the present invention) comprising:
(i) a compound comprising:
a) at least one alkoxy silane moiety; and
b) at least one moiety selected from an aromatic nitroso or an aromatic nitroso precursor and combinations thereof; and
(ii) a carrier for the compound, the carrier comprising at least 0.1% w/w water. The compound may be substantially hydrolysed.

In yet a further aspect, the present invention provides for use of an adhesive composition (according to the present invention) heated from 30 to 100° C. for bonding two substrates together, the composition (according to the present invention) comprising:
1. a compound comprising:
a) at least one alkoxy silane moiety; and
b) at least one moiety selected from an aromatic nitroso or an aromatic nitroso precursor and combinations thereof; and
2. a carrier for the compound, the carrier comprising at least 0.1% w/w water.

The composition may be heated to a temperature between 40-60° C. The composition may be heated to 50° C. The heated composition may be applied directly to the target substrate. The composition may be cooled prior to application to the target substrate.

The carrier of the composition may comprise between 0.1-100% w/w water. The carrier of the composition may comprise between 0.5-50% w/w water. The carrier may comprise between 1-20% w/w water. Suitably, a carrier comprising about 5% w/w water may substantially hydrolyse the nitrososilanes.

DETAILED DESCRIPTION

The rubber composition utilised in rubber bonding according to the present invention may further include known additives common to rubber compositions. These include reinforcing carbon blacks; inactive fillers such as calcium carbonates, chalks, talcs, or metal oxides; accelerator systems; vulcanization retarders; promoters such as zinc oxide or stearic acid; plasticizers such as aromatic, paraffinic, naphthenic and synthetic mineral oils; ageing, light-protecting ozone-protecting, fatigue, coloration, and processing auxiliaries; and sulfur. Commonly these additives may be present at a quantity of about 0.1 parts to about 80 parts per 100 parts by weight of the rubber composition.

Prior to application of the silane solution, the surface to be coated may be cleaned to allow better adhesion. For example, cleaning with solvent or alkaline material. Additionally and or alternatively, the substrate may be grit blasted. Application can then be conducted by a variety of methods, including dipping, spraying, brushing or wiping the solution onto the metal. It has been suggested that for improving rubber adhesion the coating remain partially cross-linked prior to vulcanisation. For this reason, the coating is usually air dried at room temperature as heat drying can cause a higher degree of cross-linking that will result in poorer adhesion between the rubber and the metal surface.

Compounds utilised in the compositions of the present invention were made as set out below:

Compound Synthesis

Compounds A, B, C and D (above) were synthesised according to the following experimental procedure and as illustrated in the reaction scheme above.

Reaction (1) (vide supra) was carried out as outlined in J. J D'Amico, C. C. Tung and L. A. Walker, *J. Am. Chem. Soc.*, 5957 (1959).

Reaction (2): γ-Isocyantopropyltriethoxysilane (GE Bayer Silicones A-1310) (2.35 g, 9.5 mmol) was solvated in 10 mL of anhydrous THF in a 50 mL round bottom flask. The reaction flask was flushed with nitrogen and charged with N,N-bis-(2-hydroxyethyl)-4-nitroso-aniline (2 g, 9.5 mmol), followed by a catalytic quantity of dibutyltin dilaurate (1.5 μmol). The reaction was refluxed for an additional 2 hours under nitrogen. Consumption of the isocyanate (2275 cm$^{-1}$) was monitored using infrared spectroscopy. The solvents were removed under reduced pressure to give the product in a quantitative yield.

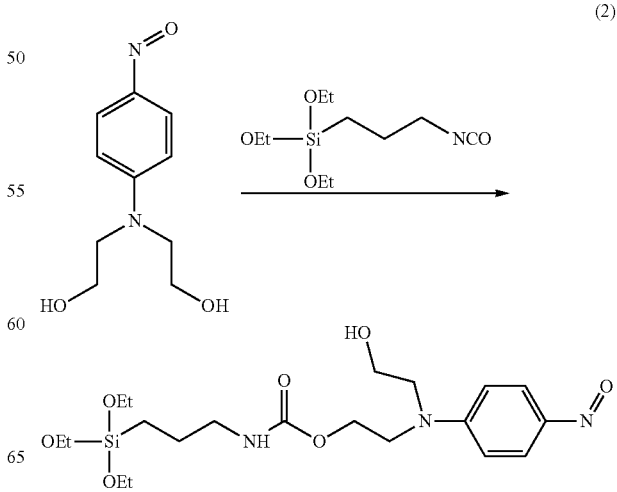

(2)

Reaction (3): γ-Isocyantopropyltrimethoxysilane (ABCR GmbH) (1.5 g, 7.3 mmol) was solvated in 8 mL of anhydrous THF in a 50 mL round bottom flask. The reaction flask was flushed with nitrogen and charged with N,N-bis-(2-hydroxyethyl)-4-nitroso-aniline (1.53 g, 7.3 mmol), followed by a catalytic quantity of dibutyltin dilaurate (1 μmol). The reaction was refluxed for an additional 2 hours under nitrogen. Consumption of the isocyanate (2275 cm$^{-1}$) was monitored using infrared spectroscopy. The solvents were removed under reduced pressure to give the product in a quantitative yield.

Reaction (4): γ-Isocyantopropyltriethoxysilane (GE Bayer Silicones A-1310) (2.35 g, 9.5 mmol) was solvated in 10 mL of anhydrous THF in a 50 mL round bottom flask. The reaction flask was flushed with nitrogen and charged with N,N-bis-(2-hydroxyethyl)-4-nitroso-aniline (1 g, 4.75 mmol), followed by a catalytic quantity of dibutyltin dilaurate (1.5 μmol). The reaction was refluxed for an additional 5 hours under nitrogen. Consumption of the isocyanate (2275 cm$^{-1}$) was monitored using infrared spectroscopy. The solvents were removed under reduced pressure to give the product in a quantitative yield.

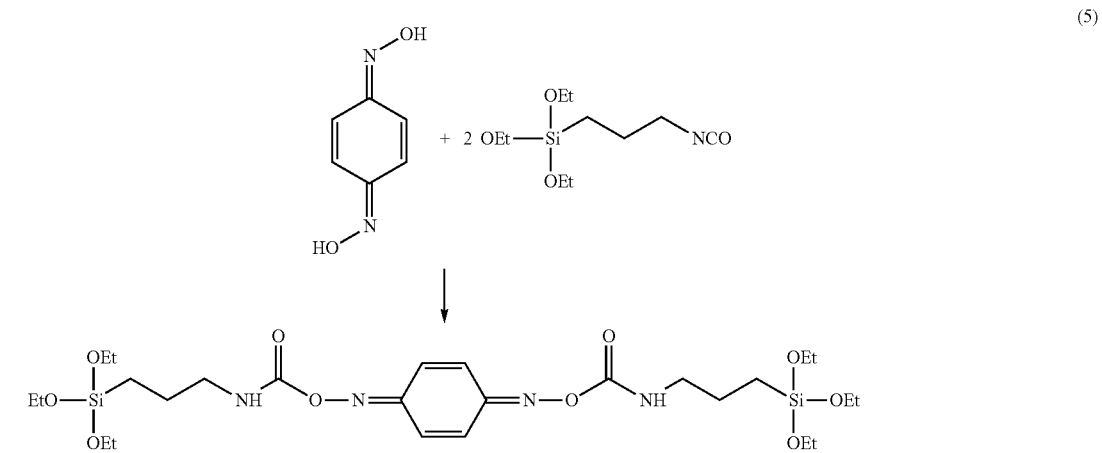

(4)

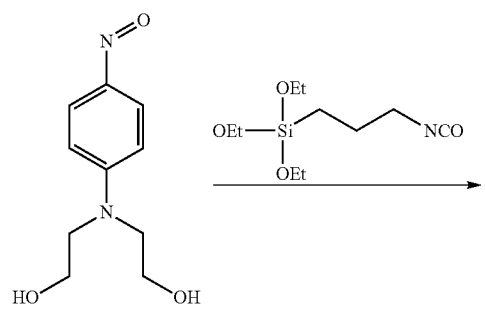

(3)

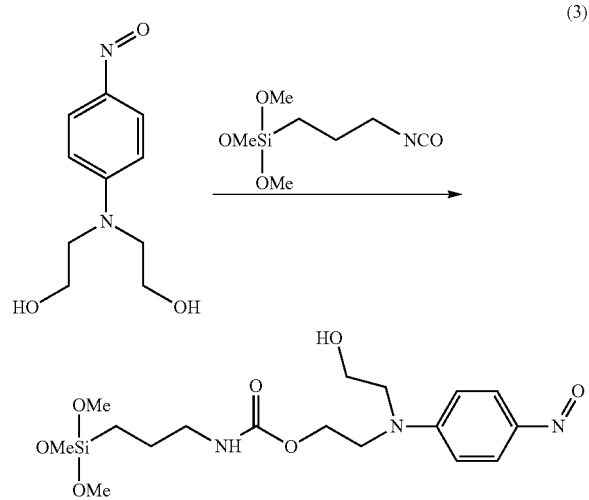

(5)

Reaction (5): γ-Isocyantopropyltriethoxysilane (GE Bayer Silicones A-1310) (10.68 g, 43.18 mmol) was solvated in 30 mL of anhydrous THF in a 100 mL round bottom flask. The reaction flask was flushed with nitrogen and charged with p-benzoquinone dioxime (Sigma-Aldrich) (3 g, 21.72 mmol), followed by a catalytic quantity of dibutyltin dilaurate (1.5 μmol). The reaction was refluxed for an additional 5 hours under nitrogen. Consumption of the isocyanate (2275 cm$^{-1}$) was monitored using infrared spectroscopy. The solvents were removed under reduced pressure to give the product in a quantitative yield.

Reaction (6): γ-Isocyantopropyltriethoxysilane (GE Bayer Silicones A-1310) (2.35 g, 9.5 mmol) was solvated in 10 mL of anhydrous THF in a 50 mL round bottom flask. The reaction flask was flushed with nitrogen and charged with 2-(N-ethylanilino)ethanol (0.78 g, 4.75 mmol), followed by a catalytic quantity of dibutyltin dilaurate (1.5 μmol). The reaction was refluxed for an additional 5 hours under nitrogen. Consumption of the isocyanate (2275 cm$^{-1}$) was monitored using infrared spectroscopy. The solvents were removed under reduced pressure to give the product in a quantitative yield.

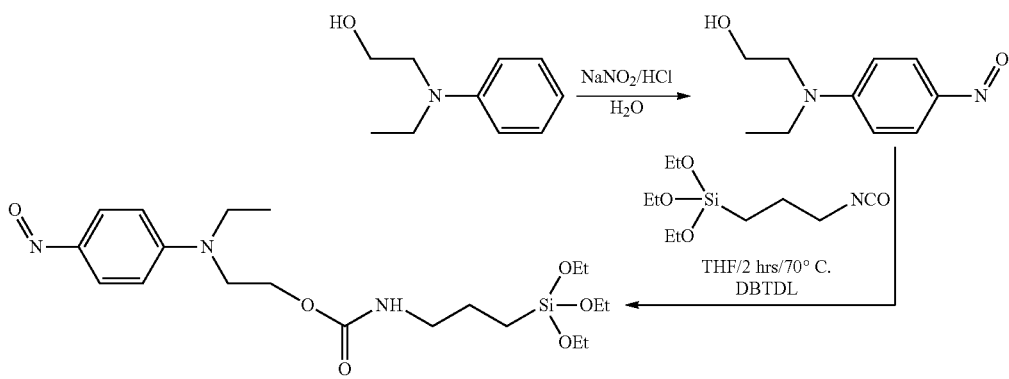

Formulations comprising the compounds of the invention were prepared as set out below.
Natural Rubber Composition—Available from Merl Ltd. (Merl Sulfur Cured NR60)
Tests were carried out using natural rubber of the following composition:

| Ingredient | Parts by weight |
|---|---|
| Natural Rubber[a] | 100 |
| Zinc Oxide | 3.5 |
| Stearic Acid | 2 |
| Carbon Black[b] | 40 |
| Naphthenic Oil (low viscosity)[c] | 5 |
| 1,2-Dihydro-2,2,4-Trimethylquinoline[d] | 2 |
| N-(1,3-dimethylbutyl)-N'-phenyl-p-phenylenediamine[e] | 1 |
| Hydrocarbon Waxes[f] | 2 |
| CBS[g] | 0.7 |
| Sulphur | 2.5 |

[a]NR SMR CV 60;
[b]SRF N762 black;
[c]Oil Strukthene 410;
[d]Flectol H;
[e]Santoflex 13 (HPPD);
[f]Sunproof Improved Wax;
[g]Vulcanisation accelerator, N-Cyclohexyl-2-benzothiazole.

EXAMPLES

The following nitrososilane was utilised in each of formulations 1 to 7:

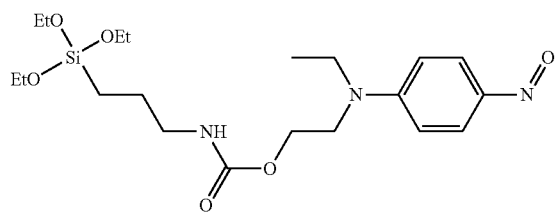

Sample Preparation and Testing

To assess the efficacy of the adhesive systems of the present invention in bonding rubbers to metal surfaces, a series of tests were performed according to the ASTM 429-B standard adjusted to a 45° angle. Grit-blasted steel laps (2.54 cm (1 inch) wide, 10.16 cm (4 inch) long panels or coupons) were coated with the adhesive composition and adhered to natural rubber in a vulcanisation process. The adhesive was applied to the steel laps without any cooling. Alternatively, the adhesive may be applied to the steel laps having been cooled to room temperature. The natural rubber compositions were sulfur-cured compositions as set out in the Formulation tables.

Before application of the adhesive, 2.54 cm (1 inch) of length and 2.54 cm wide (1 inch) on both ends of the grit-blasted steel lap were masked to prevent that region being available for bonding to the rubber, leaving a central area of 2.54 cm (1 inch) in width and 5.08 cm (2 inches) in length available to bond to the rubber.

A layer of uncured rubber was then placed on each coupon and cured in a standard hydraulic vulcanisation press for a period of time specified by the rubber's cure profile. In the case of the natural rubber used in the bonding process in the present invention, the rubber was cured for 20 minutes at 150° C. under a pressure of 20-30 Tonnes, to ensure intimate contact of the surfaces being bonded and the adhesive.

After curing the bonded samples were aged for 24 hours at room temperature before being subjected to testing and the tear pattern noted. Each sample was tested by the 45° angle modified ASTM 429-B standard using Instron equipment (Instron tester, Model No. 5500R) at a load rate of 50 mm per minute until separation is complete.

"Rubber coverage" is the percentage of rubber remaining on the bonded metal substrate after peel testing. 100% rubber failure means that the rubber completely failed with no portion of the rubber peeling away from the surface of the metal (and equates to 100% rubber failure). Generally it is desirable that the rubber substrate fails before the substrate to rubber bond fails. The results achieved with formulations according to present invention are set out below.

R—Rubber Failure

Pre-bake represents heating at the temperature at time indicated prior to vulcanisation.

Formulation 1:

| Component | % w/w |
|---|---|
| Novel nitrososilane | 10 |
| Bis(triethoxysilylpropyl)amine | 2 |
| Acetic acid | 0.4 |
| Ethanol/water (1:1) | 87.6 |
| Bond Strength = 13.9 N/mm (70% R) | |

Nitrososilane was dissolved in an ethanol/water (1:1) mixture and stirred into solution. To this bis(triethoxysilylpropyl)amine and acetic acid were added and heated to 50° C. for 2 hours.

Formulation 2:

| Component | % w/w |
|---|---|
| Novel nitrososilane | 9.5 |
| (3-Aminopropyl)triethoxysilane | 2.0 |
| N990[a] | 0.5 |
| CK3[b] | 2.0 |
| Aerosil 200[c] | 1.0 |
| Ethanol/water (95:5) | 85 |
| Bond Strength = 9.2 N/mm (85% R) | |
| Bond Strength after Pre-bake (5 min @ 160° C.) = 9.1 N/mm (85% R) | |

Nitrososilane was dissolved in an ethanol/water (95:5) mixture and stirred into solution. To this (3-Aminopropyl)triethoxysilane, CK3 carbon black, N990 carbon black and Aerosil 200 were added and heated to 50° C. for 2 hours.

Formulation 3:

| Component | % w/w |
|---|---|
| Novel nitrososilane | 8.9 |
| (3-Aminopropyl)triethoxysilane | 1.9 |
| N990[a] | 0.5 |
| Butvar B-72A[d] | 2.0 |
| Aerosil 200[c] | 1.4 |
| Ethanol/water (95:5) | 85.3 |
| Bond Strength = 10.6 N/mm (80% R) | |
| Bond Strength after Pre-bake (5 min @ 160° C.) = 10.2 N/mm (80% R) | |

Nitrososilane, (3-Aminopropyl)triethoxysilane, Aerosil 200 and ethanol/water (95:5) solution were stirred together and heated at 50° C. for 2 hours. After which time a Butvar B-72A in ethanol/water (95:5) solution was added and stirred at room temperature for 30 min. N990 was then added and stirred for 10 min before application to grit-blasted steel laps.

Formulation 4:

| Component | % w/w |
|---|---|
| Novel nitrososilane | 8.9 |
| (3-Aminopropyl)triethoxysilane | 1.9 |
| N990[a] | 0.5 |
| Butvar B-76[e] | 2.0 |
| Aerosil 200[c] | 1.4 |
| Ethanol/water (95:5) | 85.3 |
| Bond Strength = 9.3 N/mm (60% R) | |
| Bond Strength after Pre-bake (5 min @ 160° C.) = 9.9 N/mm (70% R) | |

Nitrososilane, (3-aminopropyl)triethoxysilane, Aerosil 200 and ethanol/water (95:5) solution were stirred together and heated at 50° C. for 2 hours. After which time a Butvar B-76 in ethanol/water (95:5) solution was added and stirred at room temperature for 30 min. N990 was then added and stirred for a further 10 min before application to grit-blasted steel laps.

Formulation 5:

| Component | % w/w |
|---|---|
| Novel nitrososilane | 8.5 |
| (3-Aminopropyl)triethoxysilane | 1.8 |
| CSX-691[f] | 0.5 |
| Butvar B-72A[e] | 7.1 |
| Aerosil 200[c] | 1.3 |
| Ethanol/water (95:5) | 80.8 |
| Bond Strength = 10.9 N/mm (85% R) | |
| Bond Strength after Pre-bake (5 min @ 160° C.) = 11.7 N/mm (85% R) | |

Nitrososilane, (3-aminopropyl)triethoxysilane, Aerosil 200 and ethanol/water (95:5) solution were stirred together and heated at 50° C. for 2 hours. After which time a Butvar B-72A in ethanol/water (95:5) solution was added and stirred at room temperature for 30 min. CSX-691 was then added and stirred vigorously for a further 10 min before application to grit-blasted steel laps.

Formulation 6:

| Component | % w/w |
|---|---|
| Novel nitrososilane | 8.5 |
| (3-Aminopropyl)triethoxysilane | 1.8 |
| CSX-691[f] | 0.5 |
| Butvar B-72A[e] | 2.0 |
| Aerosil 200[c] | 1.3 |
| Ethanol/water (95:5) | 85.9 |
| Bond Strength = 6.7 N/mm (60% R) | |
| Bond Strength after Pre-bake (5 min @ 160° C.) = 7.9 N/mm (60% R) | |

Nitrososilane, (3-aminopropyl)triethoxysilane, Aerosil 200 and ethanol/water (95:5) solution were stirred together and heated at 50° C. for 2 hours. After which time a Butvar B-72A in ethanol/water (95:5) solution was added and stirred at room temperature for 30 min. CSX-691 was then added and stirred vigorously for a further 10 min before application to grit-blasted steel laps.

Formulation 7:

| Component | % w/w |
|---|---|
| Novel nitrososilane | 8.9 |
| (3-Aminopropyl)triethoxysilane | 1.9 |
| Special Black 4[g] | 0.5 |
| Butvar B-72A[d] | 2.0 |
| Aerosil 200[c] | 1.4 |
| Ethanol/water (95:5) | 85.3 |
| Bond Strength = 9.4 N/mm (60% R) | |
| Bond Strength after Pre-bake (5 min @ 160° C.) = 10.0 N/mm (60% R) | |

Nitrososilane, (3-Aminopropyl)triethoxysilane, Aerosil 200 and ethanol/water (95:5) solution were stirred together and heated at 50° C. for 2 hours. After which time a Butvar B-72A in ethanol/water (95:5) solution was added and stirred at room temperature for 30 min. Special Black 4 was then added and stirred vigorously for a further 10 min before application to grit-blasted steel laps.

Formulation 8:

In this example the rubber was bonded to a glass lap/slide available from Ideal Glass Ltd.

| Component | % w/w |
|---|---|
| Novel nitrososilane | 9.5 |
| (3-Aminopropyl)triethoxysilane | 2.0 |
| N990[a] | 0.5 |
| CK3[b] | 2.0 |
| Aerosil 200[c] | 1.0 |
| Ethanol/water (95:5) | 85 |
| Bond Strength = 10.2 N/mm (85% R) | |
| Bond Strength after Pre-bake (5 min @ 160° C.) = 8.8 N/mm (80% R) | |

Nitrososilane was dissolved in an ethanol/water (95:5) mixture and stirred into solution. To this (3-aminopropyl)triethoxysilane, CK3 carbon black, N990 carbon black and Aerosil 200 were added and heated to 50° C. for 2 hours.

a. N990 is an alkaline carbon black from Cancarb International.
b. CK3 is an acidic carbon black from Evonik.
c. Aerosil 200 is a hydrophilic silica from Evonik.
d. Butvar B-72A is a polyvinyl butyral resin from Solutia Inc.
e. Butvar B-76 is a polyvinyl butyral resin from Solutia Inc. of lower viscosity than Butvar B-72A.
f. CSX-691 is an alkaline carbon black from Cabot.
g. Special Black 4 is an acidic carbon black from Evonik.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:
1. An adhesive composition comprising:
   (i) a compound comprising:
      a) at least one alkoxy silane moiety; and
      b) at least one moiety selected from an aromatic nitroso or an aromatic nitroso precursor and combinations thereof; and
   (ii) a carrier for the compound, the carrier comprising at least 0.1% water.
2. A composition according to claim 1 wherein the at least one moiety selected from an aromatic nitroso or an aromatic nitroso precursor is a nitrosobenzene or a nitrosobenzene precursor.
3. A composition according to claim 1 wherein the nitrosobenzene precursor is at least one of a quinone dioxime or a quinone oxime.
4. A composition according to claim 1 wherein said alkoxy silane moiety is of the structure:

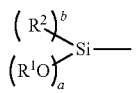

wherein 'a' can be 1-3 and 'b' can be 0-2, wherein a+b=3 and at least one alkoxy group is present;
$R^1$ can be selected from the group consisting of H, $C_1$-$C_{24}$ alkyl, $C_3$-$C_{24}$ acyl, and wherein when a 1 at least one $R^1$ is not hydrogen; and
$R^2$ can be selected from $C_1$-$C_{24}$ alkyl and $C_3$-$C_{24}$ acyl.
5. A composition according to claim 1 wherein the compound takes the form of a reaction product of an isocyanate or isothiocyanante with an active hydrogen compound.
6. A composition according to claim 1 wherein the compound is embraced by the general structure:

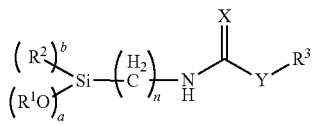

wherein n can be 1-10;
'a' can be 1-3 and 'b' can be 0-2; wherein a+b=3 and at least one alkoxy group is present;
$R^1$ can be selected from the group consisting of H, $C_1$-$C_{24}$ alkyl, $C_3$-$C_{24}$ acyl, and wherein when a 1 at least one $R^1$ is not hydrogen;
$R^2$ can be selected from $C_1$-$C_{24}$ alkyl and $C_3$-$C_{24}$ acyl;
X can be O or S;
Y can be —O—, —S—, or —NH; and
$R^3$ can be a moiety comprising nitrosoaromatic, or a nitrosoaromatic precursor.
7. A composition according to claim 6 wherein $R^3$ is a moiety comprising nitrosobenzene, quinone dioxime or quinone oxime.
8. A composition according to claim 6 wherein $R^3$ is selected from the group comprising (showing linkage through Y):

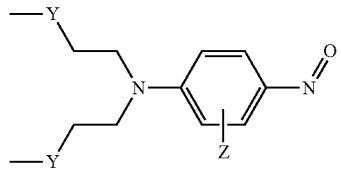

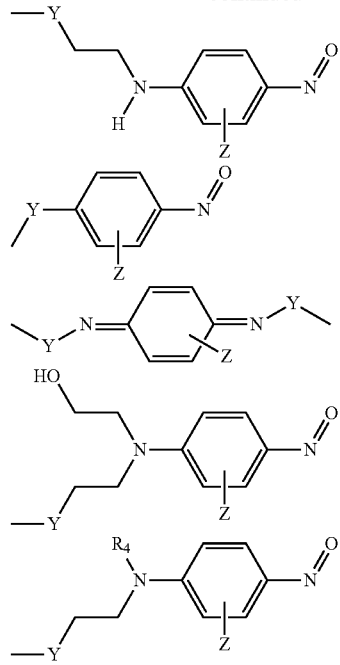

wherein $R_4$ can be $C_1$ to $C_{10}$; and
Z indicates that the rings of the above structures can optionally be mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_5$-$C_{20}$ arylamine, $C_5$-$C_{20}$ arylnitroso, amino, hydroxy, halogen and combinations thereof, and further wherein the substituents can either be the same or different on each carbon atom of the ring.
9. A composition according to claim 1 wherein the compound is of the general structure:

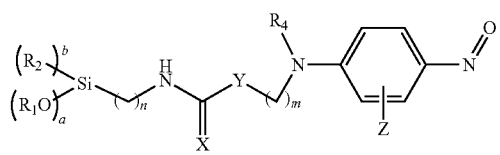

wherein 'a' can be 1-3 and 'b' can be 0-2; wherein a+b=3 and at least one alkoxy group is present;
$R^1$ can be selected from the group consisting of H, $C_1$-$C_{24}$ alkyl, $C_3$-$C_{24}$ acyl, and wherein when a≧1 at least one $R^1$ is not hydrogen; and
$R^2$ can be selected from $C_1$-$C_{24}$ alkyl and $C_3$-$C_{24}$ acyl;
m and n can be the same or different and can be 1-10;
X can be O or S;
Y can be —O—, —S—, or —NH;
$R_4$ can be $C_1$ to $C_{10}$; and
Z indicates that the rings of the above structures can optionally be mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_5$-$C_{20}$ arylamine, $C_5$-$C_{20}$ arylnitroso, amino, hydroxy, halogen and combinations thereof, and further wherein the substituents can either be the same or different on each carbon atom of the ring.
10. A composition according to claim 1 wherein the compound is of the general structure:

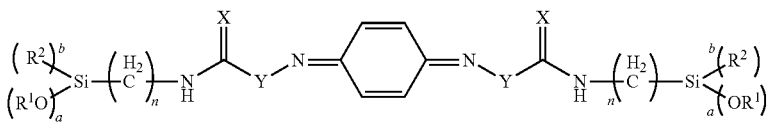

wherein n can be 1-10;
'a' can be 1-3 and 'b' can be 0-2; wherein a+b=3 and at least one alkoxy group is present;
$R^1$ can be selected from the group consisting of H, $C_1$-$C_{24}$ alkyl, $C_3$-$C_{24}$ acyl, and wherein when a≧1 at least one $R^1$ is not hydrogen;
$R^2$ can be selected from $C_1$-$C_{24}$ alkyl and $C_3$-$C_{24}$ acyl;
X can be O or S; and
Y can be —O, —S, or —$NH_x$, wherein x=1 or 2.

11. A composition according to claim 1 wherein the compound is of the general structure:

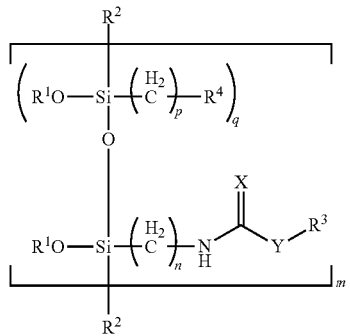

wherein m can be 1-100; n can be 1-10; p can be 1-10; q can be 0-50; and if q=0, m≧0.2;
$R^1$ can be selected from the group consisting of H, $C_1$-$C_{24}$ alkyl, $C_3$-$C_{24}$ acyl;
$R^2$ can be selected from the group consisting of $OR^1$, $C_1$-$C_{24}$ alkyl and $C_3$-$C_{24}$ acyl, and wherein when $R^2$=$OR^1$ at least one $R^1$ is not hydrogen;
$R^4$ can be selected from the group consisting of acrylate, aldehyde, amino, anhydride, azide, maleimide, carboxylate, sulphonate, epoxide, ester functional, halogens, hydroxyl, isocyanate or blocked isocyanate, sulphur functional, vinyl and olefin functional, or polymeric structures;
X can be O or S;
Y can be —O, —S, or —$NH_x$ (where x=1 or 2); and
$R^3$ can a moiety comprising nitrosoaromatic, or a nitrosoaromatic precursor.

12. A composition according to claim 11 wherein $R^3$ is a moiety comprising nitrosobenzene, quinone dioxime or quinone oxime.

13. A composition according to claim 1 wherein said compound can react in-situ to form one of a nitrosobenzene moiety, a dinitrosobenzene moiety, or a para-nitrosophenol moiety.

14. A method of bonding two substrates together, the method comprising:
(i) substantially hydrolysing a compound comprising:
   a) at least one alkoxy silane moiety; and
   b) at least one moiety selected from an aromatic nitroso or an aromatic nitroso precursor and combinations thereof;
(ii) applying the substantially hydrolysed compound of step (i) to at least one substrate; and
(iii) mating the first and second substrates so as to form a bond therebetween.

15. A method of bonding two substrates together, the method comprising:
A. providing a composition comprising:
   (i) a compound comprising:
      a) at least one alkoxy silane moiety; and
      b) at least one moiety selected from an aromatic nitroso or an aromatic nitroso precursor and combinations thereof; and
   (ii) a carrier for the compound, the carrier comprising at least 0.1% water;
B. heating the composition; and
C. applying the composition to a bonding surface of at least one of the substrates and bringing the bonding surfaces of the substrates together.

16. A process for using an adhesive composition comprising the steps of:
A. Providing two substrates having matable surfaces
B. Providing a composition, said composition comprising:
   (i) a compound comprising:
      a) at least one alkoxy silane moiety; and
      b) at least one moiety selected from an aromatic nitroso or an aromatic nitroso precursor and combinations thereof; and
   (ii) a carrier for the compound, the carrier comprising at least 0.1% water;
C. Providing said composition on at least one matable surface of at least one substrate or between the matable surfaces of the two substrates; and
D. Exposing the composition to temperature conditions in the range of from 30 to 100° C.

* * * * *